United States Patent [19]
Kobren et al.

[11] Patent Number: 5,788,716
[45] Date of Patent: Aug. 4, 1998

[54] SURGICAL INSTRUMENT AND METHOD FOR FALLOPIAN TUBE LIGATION AND BIOPSY

[76] Inventors: Myles S. Kobren, 100 Manetto Hill Rd. - Suite 302, Plainview, N.Y. 11803; Joseph C. Segen, 1 Hawthorne La., Manhasset, N.Y. 11030

[21] Appl. No.: 782,278

[22] Filed: Jan. 13, 1997

[51] Int. Cl.[6] .................................................. A61B 17/04
[52] U.S. Cl. .................................................. 606/141; 606/142
[58] Field of Search ......................... 606/140, 141, 606/151, 157, 158, 142; 128/831

[56] References Cited

U.S. PATENT DOCUMENTS 5,190,560  3/1993  Woods et al. ..................... 606/137
5,217,473  6/1993  Yoon ................................. 606/141
5,226,908  7/1993  Yoon ................................. 606/141

*Primary Examiner*—Gary Jackson
*Attorney, Agent, or Firm*—Eliot S. Gerber

[57] ABSTRACT

A laparoscopic surgical instrument to perform tubular ligation of the Fallopian tube includes a handle grip to be held by the surgeon. A finger grip is used to slide a body member on a rod fixed to the handle and to squeeze a staple onto the Fallopian tube. A forceps, operated by a button on the handle, pulls up the Fallopian tube and holds a segment of the tube, as a biopsy sample, after it has been severed.

15 Claims, 5 Drawing Sheets

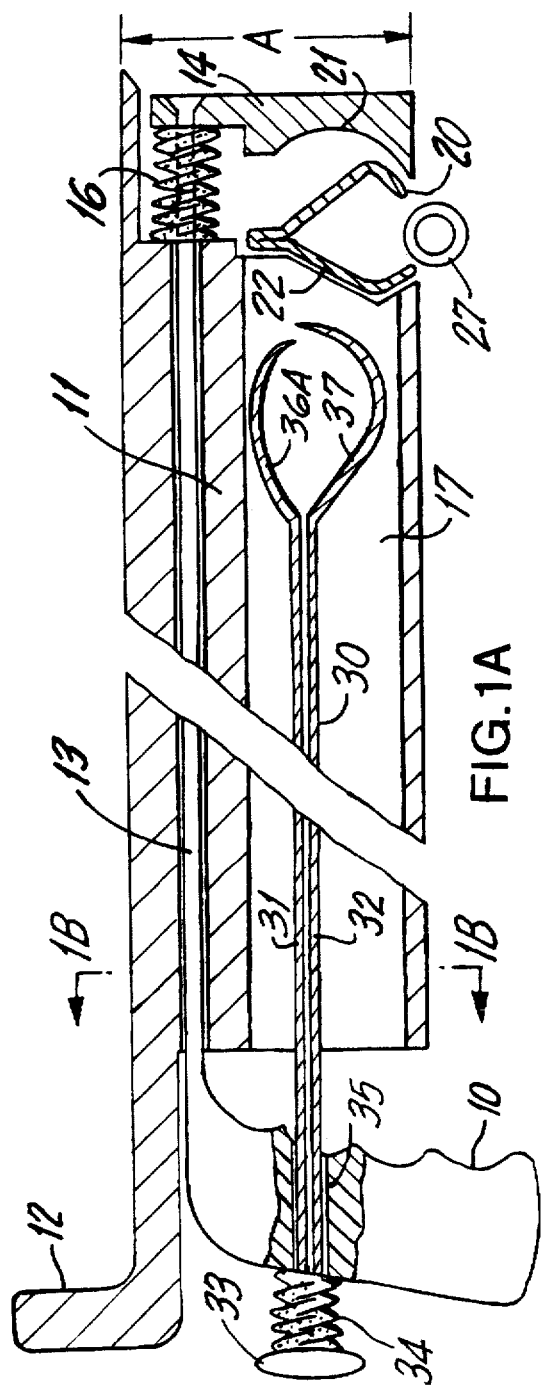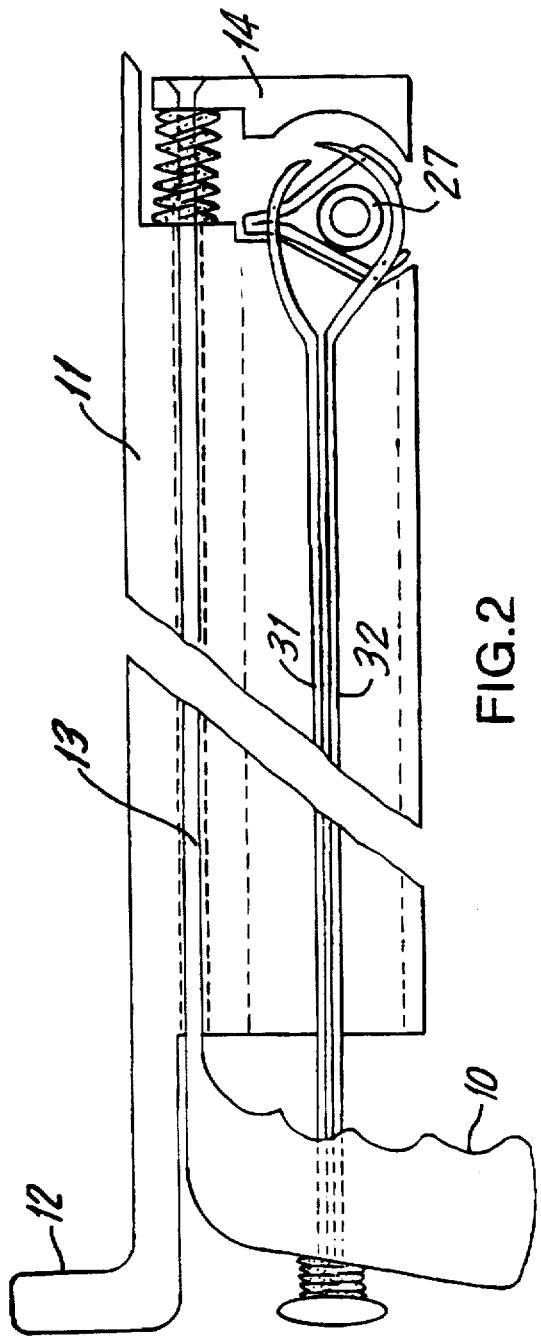

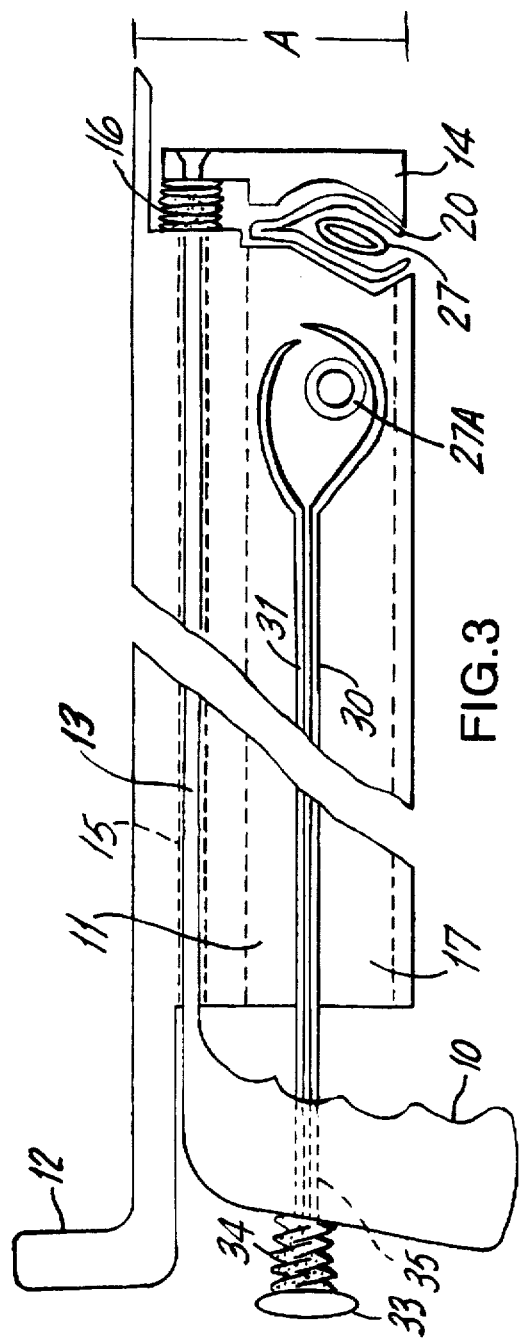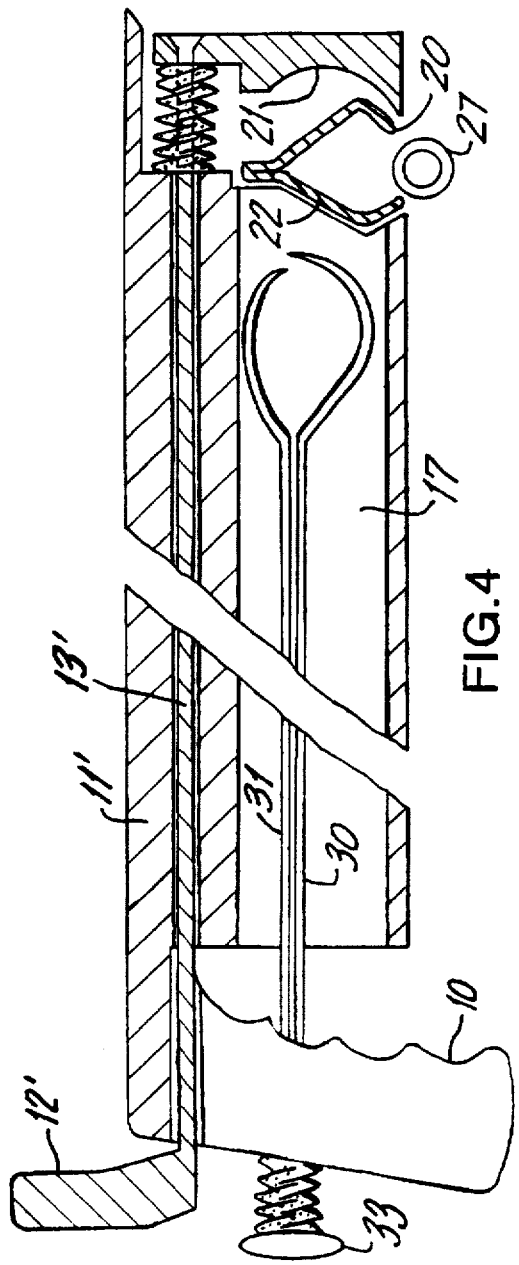

SURGICAL INSTRUMENT AND METHOD FOR FALLOPIAN TUBE LIGATION AND BIOPSY

FIELD OF THE INVENTION

The field of the invention is medical devices and more specifically surgical instruments and methods for the ligation and biopsy of Fallopian tubes.

BACKGROUND OF THE INVENTION

During each menstrual cycle, one ovary releases an egg. The egg travels through the Fallopian tube to the uterus. One way to effect sterilization in women is to cut and tie Fallopian tubes. An alternative is to use an instrument with which the Fallopian tubes are electrically cauterized and coagulated. That is a presently widely used surgical procedure called "laparoscopic tubular sterilization" (viewing with a laparoscope). The terms "laparoscopic" and "endoscopic" refer to minimally invasive surgical procedures in which instruments such as cutters, retractors, suture tie devices, forceps, etc., are introduced through a small tube (trochar sleeve) which has been inserted through the patient's skin. The surgical site is viewed with a laparoscope, which is an optical device generally using optic fibers, introduced through, or in place of, the tube (trochar sleeve) and may be used to perform video surgery. The terms "tubular ligation" and "tubular sterilization" refer to cutting or closing the Fallopian tubes.

At present, the surgeon will use a trochar to form an entrance hole through the patient's skin. Its tubular portion, 5 mm (millimeters) to 15 mm and typically 10 mm in diameter of its internal bore, will be left in place so that instruments may be inserted, and withdrawn, therethrough. A forceps (gripping or holding device) is introduced through the trochar tube to elevate the Fallopian tube and to cauterize the tube. Such cauterization uses high voltage and performs two functions, namely (1) it severs the tube and (2) it prevents blood flow from the two severed ends by coagulation.

However, such cauterization may have serious adverse side effects, due to sparks from high voltage. For example, a burn or hole may accidentally be formed in adjacent organs. Such burns may not be apparent at the time of the operation, but may later cause complications, requiring treatment and further surgery. Burns arising from tubal coagulation are an important cause of medical malpractice actions.

In addition, the surgeon, by accident, may cauterize the round ligament, which looks like the Fallopian tube. Since there is no tissue sample (biopsy) obtained, there is no positive way of knowing that the operation closed the Fallopian tube and not the round ligament.

A commonly used instrument for such laparoscopic tubular ligations is the "bipolar forceps for tubal coagulation" available from ELMED (Germany). It is available in 30 cm and 44 cm lengths and provides a forceps with two fingers (extensions) through which electrical current is passed.

In U.S. Pat. No. 5,336,231 to Adair, a laparoscopic surgical device positions a tissue and ligates the tissue using a loop of suture material. An electrical wire in the form of a hook coagulates the ligated tissue and a cutting blade is used to cut the tissue.

U.S. Pat. No. 4,325,377 to Boebel relates to a surgical forceps that applies a clip to a Fallopian tube during a tubal ligation. The forceps may be inserted through a trochar sleeve.

U.S. Pat. No. 4,869,268 to Yoon describes a multipurpose surgical device for occluding an anatomical tube, such as a Fallopian tube. In one embodiment it applies a stretchable clip to the tube. A forceps for taking a biopsy is also disclosed, as a separate instrument.

U.S. Pat. No. 3,834,392 describes a system in which a flexible forceps is inserted through a laparoscope to close the Fallopian tube either by electrical oscillations or a clamp.

SUMMARY OF THE INVENTION

In accordance with the present invention there is provided a Fallopian tube stapling, cutting and biopsy instrument. The instrument operates without electricity, so there is no danger of burns to adjacent tissue caused by sparks from high voltage. It acts as a biopsy instrument and retrieves a tissue sample from the surgical site, which may be analyzed in a laboratory to insure that the Fallopian tube was cut, and not the patient's round ligament. The instrument is sufficiently small in diameter, less than 10 mm, so that it may be inserted and operated within a trochar sleeve or a laparoscopic device.

The instrument has a grip handle at its proximate end which is held in the surgeon's hand, the "surgeon" being the gynecologist or other user. It also has a finger grip and a button which are adapted to be operated by the surgeon's fingers. The finger grip is connected to a body member which slides on a rod fixed to the handle grip. A clamp member is fixed on the end of the rod and an inverted "U" shaped staple (clamp) is positioned between the distal end of the body member and the clamp member. A forceps, attached to the button, is advanced so that its fingers are positioned around the Fallopian tube. Then the staple is dropped over the Fallopian tube and the body member is advanced to close the staple on the Fallopian tube. A cutting member is then advanced and severs the Fallopian tube at two separated places. The instrument is then withdrawn from the patient with a severed segment of the Fallopian tube held by the fingers of the forceps for later laboratory analysis.

The instrument has pulled up the Fallopian tube using the forceps' fingers; placed and closed a staple on the Fallopian tube to prevent bleeding; cut the Fallopian tube in two places; and removed the severed Fallopian tube segment for laboratory analysis.

BRIEF DESCRIPTION OF THE DRAWINGS

The accompanying drawings show preferred embodiments of the present invention and should be considered along with the detailed description. In the drawings:

FIG. 1A is a side cross-sectional view of the first embodiment of the present invention in its non-deployed position, i.e., the distal end is at the surgical site but the Fallopian tube has not yet been lifted by the forceps;

FIG. 2 is a side cross-sectional view of the embodiment of FIG. 1A in its deployed position in which the forceps has lifted the Fallopian tube but the staple (clamp) has not yet been closed;

FIG. 3 is a side cross-sectional view of the embodiment of FIG. 1A in its closed position in which the staple has been closed and a segment of the severed Fallopian tube is grasped by the forceps as a biopsy sample;

FIG. 4 is a side cross-sectional view of the second embodiment of the present invention in its non-deployed position.

DETAILED DESCRIPTION

Figure 1B:
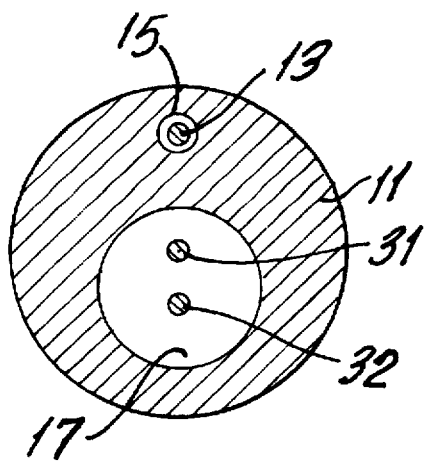
FIG. 1B is a cross-sectional view taken along line B—B looking in the direction of the arrows.

As shown in FIG. 1A, the surgical instrument of the present invention includes a handle grip 10 at its proximate end. The other portions, for clarity of illustration, are shown in some figures as being enlarged. However, the entire body member 11 in its vertical dimension (arrow A) is preferably about 10 mm (millimeters) so that it fits within a trochar sleeve.

The embodiments of FIGS. 1-4, for simplicity of illustration, do not show a cutting mechanism. However, it will be understood that each includes a cutting mechanism, for example, of the types shown in FIGS. 7-8B.

The body member 11 has an upraised finger grip 12 which is adapted to be pushed and pulled by a surgeon's finger. The handle grip 10 is fixed to, or integral with, a rod 13. A fixed clamp member 14 is fixed at the end of rod 13 at the distal end of the instrument.

The body member 11 has an internal tubular bore 15 which fits over the rod 13 so that the body member 11 may be slidingly advanced, and retracted, on the rod 13. A spring 16 around the rod 13 is positioned between the clamp member 14 and the body member 11 to normally urge the body member toward the handle grip 10 (left in FIG. 1A).

A staple (clip) 20 is held in between the curved face 21 of clamp member 14 and the angled distal face 22 of the body member 11.

Figure 5A:
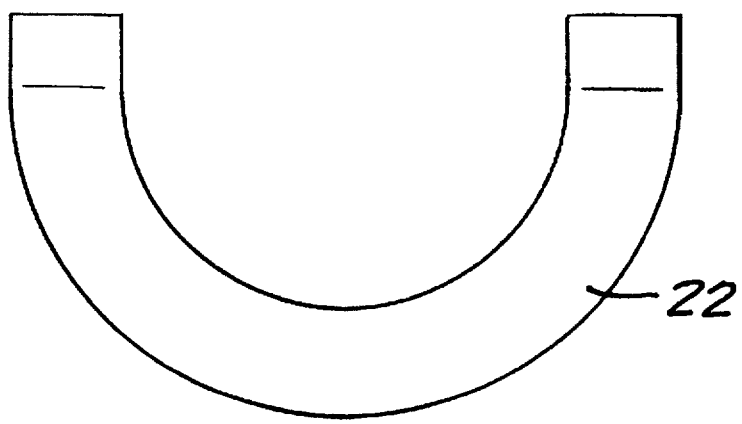
FIG. 5A is an enlarged front view of the staple (clamp)
Figure 5B:
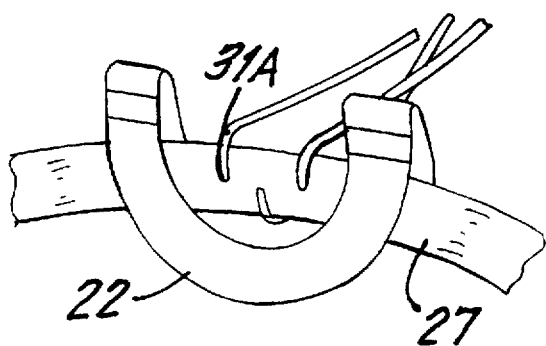
FIG. 5B is a perspective view of the staple.
Figure 6:
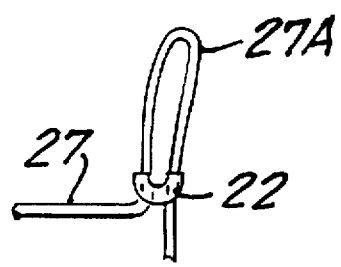
FIG. 6 shows the clamp closed on a Fallopian tube before the tube is severed.

The staple 20, as shown in FIG. 5, is preferably a biocompatible metal or plastic having a non-elastic property. A generally curved U-shaped member 25 is integral with a similarly curved U-shaped member 26. The staple 20 closes the Fallopian tube 27 by squeezing it at two locations 28 and 28. The staple initially, in the non-deployed position, has its arms 25 and 26 separated, see FIG. 1. In the deployed position, shown in FIG. 2, the open staple 20 is dropped over the Fallopian tube 27. Then, as shown in FIG. 3, the clamp member 14 is pulled to its closed position (left in FIG. 3), against spring 16, by pulling on grip 12. The staple is closed by being squeezed between fixed clamp member and movable body member 11. The staple, when it is squeezed closed, stays in its closed shape.

A forceps 30 is used to grasp the Fallopian tube 27, raise the tube 27, position it so that the staple 20 may be dropped over it and retrieve a small segment of the tube 27 as a biopsy sample, see FIG. 3. The forceps 30 comprises an elongated top arm 31 and an elongated bottom arm 32. The arms, at their proximate ends, are secured in button 33 which is spring-loaded by spring 34. The spring 34 normally urges button 33 away from handle 10 (left in FIGS. 1A, 2-4). The forceps arms 31,32 slide within a second bore 17, of body member 11, which is larger in diameter than bore 15. The arms 31,32 extend through a bore 35 (channel) in handle grip 10 and extend into the body member 11. The arm 32, at its distal end, has curved fingers 36A, 36B and the arm 30, at its distal end, has curved finger 37. When the instrument is moved from its non-deployed position (FIG. 1A) to its deployed position (FIG. 2) the button 33 is pushed, compressing spring 34 and extending the fingers 36A, 36B, 37 around the Fallopian tube 27.

Figure 1C:
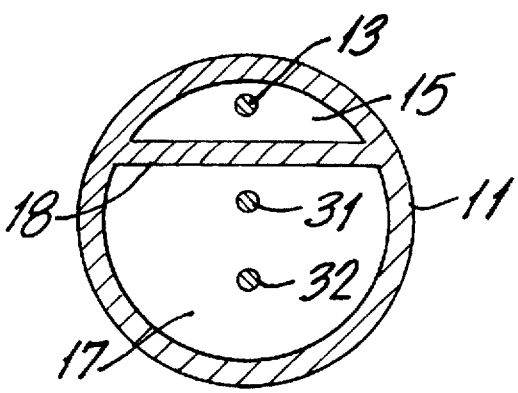
FIG. 1C is a cross-sectional view of an alternative embodiment.

In the embodiment shown in FIG. 1B the body member 11 is a solid member having bores 15 and 17 therethrough. In the embodiment of FIG. 1C the body member 11 is tubular and a separator 18 separates bore 15 from bore 17.

In the embodiment of FIG. 4 the body member 11' is fixed to the handle grip and the clamp member 14' is fixed to the rod 13'. The rod 13' has a finger grip extension 12'. When the rod 13' is pulled by its extension 12' the clamp member 14' squeezes the staple 20 closed.

Figure 7:
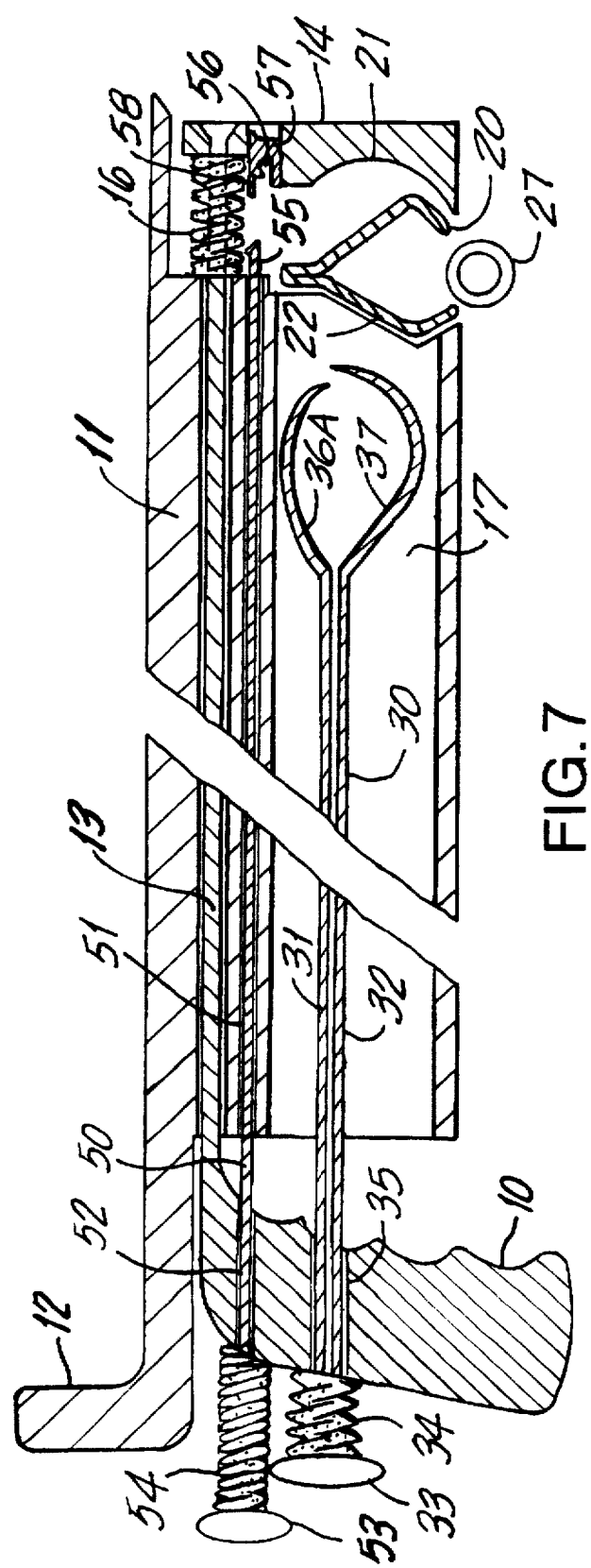
FIG. 7 is a side cross-sectional view similar to FIG. 4 but also showing the cutting mechanism.

As shown in FIG. 7 the cutting mechanism, in this embodiment, comprises an elongated rod 50 which fits in bore 51 of body member 11. At its proximal end the rod 50 passes through the bore 52 of handle 10 and is fixed to button 53. The button 53 is spring-loaded by spring 54. The rod has a fish-hook-like end 55. That end, when advanced by pushing on the button 53, catches in cavity 56 of blade member 57. The blade member 57 sides within a slot and carries a cutting blade 58.

Figure 8A:
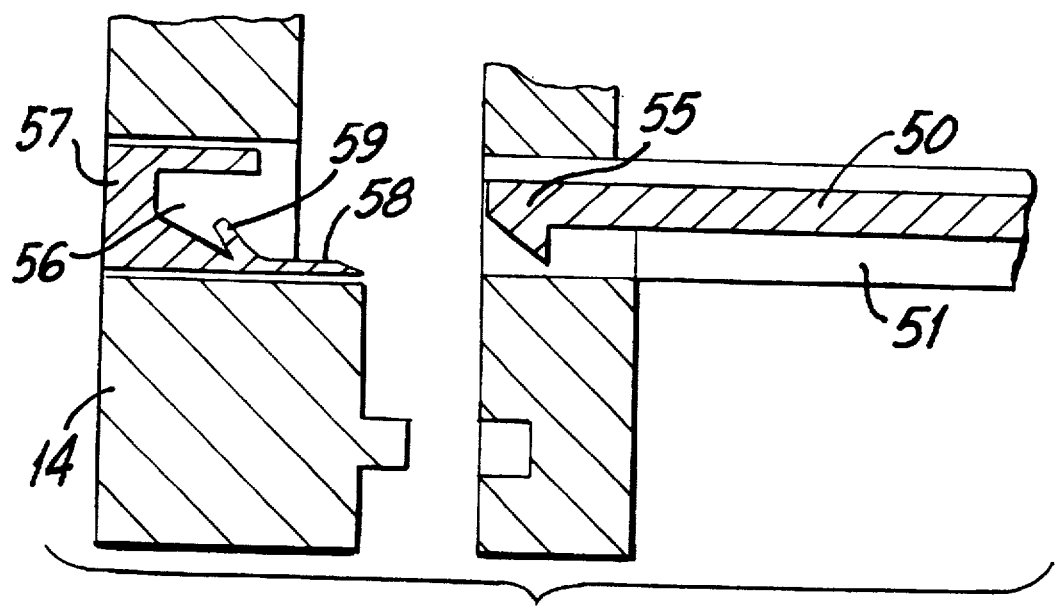
FIGS. 8A and 8B are enlarged cross-sectional views of alternative cutting mechanisms.
Figure 8B:
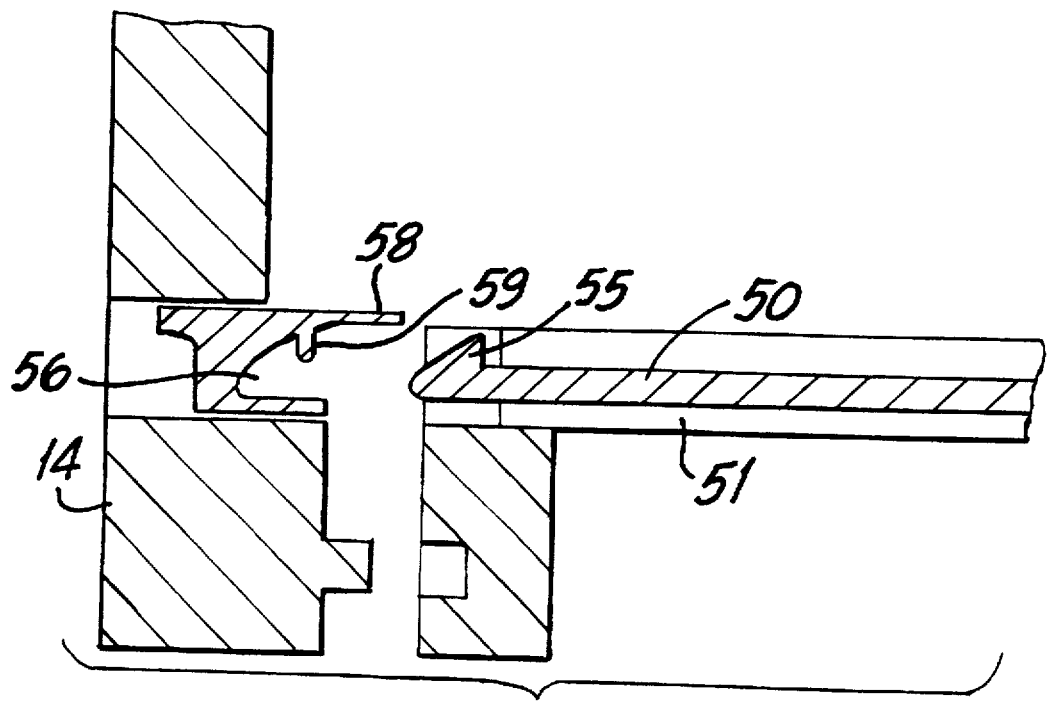

As shown in FIGS. 8A and 8B, the end 55, when advanced to within the cavity 56, is held and retained therein by flexible flange 59. The rod 50, when pulled in the proximal direction (left in FIG. 7) pulls the blade 58 and thereby cuts the Fallopian tube.

Other alternative cutting mechanisms may be used, including:

(1) The blade 58 is advanced by being attached to a pivotable link. The end of the link is pushed by a flat or curved end of rod 50. The link pivots and advances the blade.

(2) The blade is fixed on a block which is moved by a spring. The spring is held compressed until released by a detent. The detent is operated by advancing the rod 50. Other cutting mechanisms, such as scissor-like devices, are also within the scope of the present invention and the claims.

After the Fallopian tube is severed in two places, as described below, the severed section is retained between the fingers 36A, 36B, 37. When the tubular ligation procedure is completed the instrument, along with the severed Fallopian tube section, is removed. The tube section is then removed from the fingers 36A, 36B, 37 and analyzed in a laboratory to insure that it was the Fallopian tube that was cut and not the patient's round ligament.

What is claimed is:

1. A surgical instrument for the laparoscopic tubular ligation of Fallopian tubes, being an elongated instrument having a proximal and a distal end which comprises:
   (a) a handle grip at the proximal end;
   (b) a rod having a proximal and a distal end and being fixed to the handle grip at the rod's proximal end;
   (c) a clamp member fixed to the rod at the rod's distal end;
   (d) an elongated body member whose width is less than 15 millimeters and having a bore therethrough; wherein the rod is positioned within the bore;
   (e) a forceps at least partly within the body member, the forceps having a distal end and a proximal end and having fingers at the forceps' proximal end which are adapted to fit around and hold a segment of the Fallopian tube;
   (f) a staple removably held between the body member and the clamp member, the staple being sufficiently inelastic to retain a closed form upon being squeezed closed and adapted to be closed on the Fallopian tube when squeezed therebetween; and (g) cutting means within said body member to sever the Fallopian tube in two locations after the staple has been closed.

2. A surgical instrument as in claim 1 wherein the body member has a second bore and part of the forceps slides within the second bore.

3. A surgical instrument as in claim 1 wherein the staple is a "U" shaped member.

4. A surgical instrument as in claim 1 wherein the proximal end of the forceps is fixed to a button, the button being mounted proximate the handle grip and spring-loaded so that the forceps is normally urged in the proximate direction.

5. A surgical instrument as in claim 1 wherein and a spring positioned on the rod between the body member and the clamp member.

6. A surgical instrument as in claim 1 wherein the cutting means has a "U" shaped blade.

7. A surgical instrument for the laparoscopic tubular ligation of a Fallopian tube, being an elongated instrument having a proximal and a distal end which comprises:

(a) a handle grip at the proximal end;

(b) a rod having a proximal and a distal end;

(c) a clamp member fixed to the rod at the rod's distal end;

(d) an elongated body member whose width is less than 15 millimeters and having a bore therethrough;

(e) a staple which is sufficiently inelastic to retain a closed form upon being squeezed closed, the staple being removably held between the body member and the clamp member and adapted to be closed on the Fallopian tube when squeezed therebetween;

(f) forceps at least partly within the body member, the forceps having a distal and a proximal end and having fingers at the forceps' proximal end which are adapted to fit around and hold a segment of the Fallopian tube; and (g) cutting means within said body member to sever the Fallopian tube in two locations after the staple has been closed thereon.

8. A surgical instrument as in claim 7 wherein the body member is fixed onto the handle grip and the instrument includes means to move the rod relative to the body member.

9. A surgical instrument for the laparoscopic tubular ligation of Fallopian tubes, being an elongated instrument having a proximal end and a distal end to be positioned at a surgical site, the instrument comprising, as connected portions of the instrument:

(a) a handle grip means at the proximal end to be gripped by a surgeon;

(b) a clamp member at the instrument's distal end;

(c) an elongated body member whose width is less than 15 millimeters and having a bore therethrough;

a staple means having open and closed positions to clamp the Fallopian tube closed in two locations, the staple means being sufficiently inelastic to retain a closed form upon being squeezed closed and removably held between the body member and the clamp member, the staple being closed on the Fallopian tube when squeezed therebetween;

(e) a forceps having a distal end and a proximal end and having finger means within the bore and at the forceps' proximal end to fit around and hold a segment of the Fallopian tube; and (f) cutting means within said body member to sever the Fallopian tube in two locations on opposite sides of the finger means.

10. A surgical instrument as in claim 9 wherein the body member has a second bore and part of the forceps slides within the second bore.

11. A surgical instrument as in claim 9 wherein the staple means is a "U" shaped member.

12. A surgical instrument as in claim 9 wherein the proximal end of the forceps is fixed to a button mounted proximate the handle grip means and spring-loaded so that the forceps is normally urged toward the proximate direction.

13. A surgical instrument as in claim 9 and a spring positioned between the body member and the clamp member.

14. A surgical instrument as in claim 9 wherein the cutting means has a "U" shaped blade.

15. A surgical method for the tubular ligation of a Fallopian tube, the method comprising the steps of:

(a) forming an incision in the skin of the patient using a trochar having a trochar sleeve;

(b) inserting an elongated instrument to the surgical site through the trochar sleeve;

(c) positioning a staple near the distal end of the instrument, the staple being sufficiently inelastic to retain a closed form upon being squeezed closed;

(d) manipulating the forceps within the instrument to grasp and lift the Fallopian tube;

(e) using the instrument to place the staple over the grasped Fallopian tube and to squeeze the staple closed so that its arms close the Fallopian tube in two separated locations;

(f) manipulating a cutting device within the instrument to sever the Fallopian tube forming a free segment of the Fallopian tube which is held by the forceps' fingers; and (g) removing the instrument form the patient, removing the segment from the instrument, and analyzing the segment to determine if it is tissue from the Fallopian tube.

* * * * *